United States Patent [19]
Shipp

[11] Patent Number: 6,162,194
[45] Date of Patent: Dec. 19, 2000

[54] SURGICAL IRRIGATION APPARATUS AND METHODS FOR USE

[75] Inventor: John I. Shipp, Tullahoma, Tenn.

[73] Assignee: Apollo Camera, LLC, Tullahoma, Tenn.

[21] Appl. No.: 09/081,797

[22] Filed: May 20, 1998

[51] Int. Cl.[7] .................................................. A61M 1/00
[52] U.S. Cl. ............................................. 604/151; 604/31
[58] Field of Search ...................................... 604/31, 151

[56] References Cited

U.S. PATENT DOCUMENTS

| | | | |
|---|---|---|---|
| 5,270,005 | 12/1993 | Raible ........................................ | 422/46 |
| 5,376,114 | 12/1994 | Jarvik ......................................... | 623/3 |
| 5,393,207 | 2/1995 | Maher et al. ........................... | 417/423.7 |
| 5,464,391 | 11/1995 | DeVale ....................................... | 604/67 |
| 5,484,402 | 1/1996 | Saravia et al. ............................. | 604/35 |
| 5,807,313 | 9/1998 | Delk et al. ................................. | 604/35 |

FOREIGN PATENT DOCUMENTS

| | | | |
|---|---|---|---|
| 196822 | 10/1986 | European Pat. Off. .................. | 604/31 |
| 301641 | 6/1981 | Germany .................................. | 604/31 |

OTHER PUBLICATIONS

"5885XL Rechargeable Razor with Reflex Action Shaving System" (Norelco Brochure), 1996.

*Primary Examiner*—Jeffrey A. Smith
*Attorney, Agent, or Firm*—Waddey & Patterson

[57] ABSTRACT

A surgical irrigation apparatus includes a disposable assembly and a reusable assembly. The disposable assembly includes an irrigation fluid pump and a handpiece having a supply passage for delivery of irrigation fluid to the surgical site. The re-usable assembly includes a motor and a power source. The power is transferred from the motor to the pump with a magnetic coupler or other suitable device. The re-usable assembly is isolated from irrigation fluid in the disposable assembly. All of the electrical components of the apparatus are contained in the re-usable assembly. There are no electrical components in the disposable assembly. A sterile disposable assembly may be assembled in the operating room with an unsterilized re-usable assembly.

31 Claims, 5 Drawing Sheets

SURGICAL IRRIGATION APPARATUS AND METHODS FOR USE

BACKGROUND OF THE INVENTION

1. Field of The Invention

The present invention relates generally to the field of surgical suction and irrigation apparatus, and more particularly but not by way of limitation, to such an apparatus adapted for use in endoscopic surgery.

2. Description of the Prior Art

The use of suction and irrigation devices and many improvements thereof for both open and laproscopic surgery are well known in the art. U.S. Pat. No. 5,484,402 describes such an improved device whereby irrigation fluid is pumped from a source such as a saline bag through a cannula housed in a hand-held probe which is inserted through a trocar for supplying irrigation during laproscopic surgery. The liquid flow is controlled by a valve in the handpiece which also contains electrical contacts that starts the pump simultaneous with the valve opening by completing a circuit connecting a battery pack to the pump motor. Thus, pressurized irrigant is delivered to the surgical field. The switch associated with the irrigation valve is connected by a two conductor electrical cable to the pumping system which contains the battery, motor, and pump housing. Removal of the irrigant, blood, and other such matter is accomplished by opening a second valve in the handpiece thereby connecting a second cannula in the probe to a vacuum source such as a standard hospital vacuum outlet.

The irrigant and all the elements of the system that comes into contact with the surgical field must be sterile. The system described in U.S. Pat No. 5,484,402 is a single use device, all components of which are disposed of after each procedure. This is usually necessary for such devices because of the cost and difficulty encountered in decontamination and re-sterilization. Hoses and cannula offer particular difficulty in that regard. While the above-described prior art is very useful, it suffers from the fact that it is too expensive owing to the design details and the disposability issue.

What is needed then is an irrigation/suction system that is inexpensive to manufacture and one that reuses as many of the parts as is practical, combining single use inexpensive parts with multi-use parts that, preferably, do not require decontamination or sterilization prior to the next procedure.

SUMMARY OF THE INVENTION

The present invention constitutes an irrigation and suction system for use in open and laproscopic surgery such that the principal components, the pump motor and its power source, preferably a battery, is re-usable, without the need for sterilization. Additionally, the present invention eliminates the need for a switch in the handpiece or an electrical cable connecting it to the battery and pump motor. This provides the advantage, as compared to the device of U.S. Pat. No. 5,484,402, of eliminating the need for electrical wiring running to the handpiece. This greatly simplifies the set-up of the device in the operating room environment as no external power is required. The present invention senses that the valve has been opened, preferably by sensing irrigant flow through the system owing to gravity. The flow indicator signal is then used to turn on the pump to place the irrigant under pressure. Lack of a flow indication signal is then used to turn off the pump motor.

The preferred embodiment is powered by a primary cell which is switched onto the pump motor in response to a microprocessor output which is in turn activated by the flow detector. A timer in the microprocessor keeps track of the battery use time and displays, preferably, on a liquid crystal display, the number of procedures remaining prior to battery depletion.

Thus, it is an object of the invention to provide a surgical irrigation apparatus having a disposable assembly and a re-usable assembly so that a substantial portion of the apparatus can be reused thus making the system more economical than previous systems.

Another object of the present invention is the provision of a surgical irrigation apparatus having a hand actuatable valve and designed to initially supply fluid by gravity flow and to then rapidly detect the gravity flow and turn on a pump motor to provide pressurized fluid in response to the manual actuation of the valve.

Numerous other objects, features and advantages of the present invention will be readily apparent to those skilled in the art upon the reading of the following disclosure when taken in conjunction with the accompanying drawings.

DETAILED DESCRIPTION OF THE PREFERRED EMBODIMENTS

Figure 1:
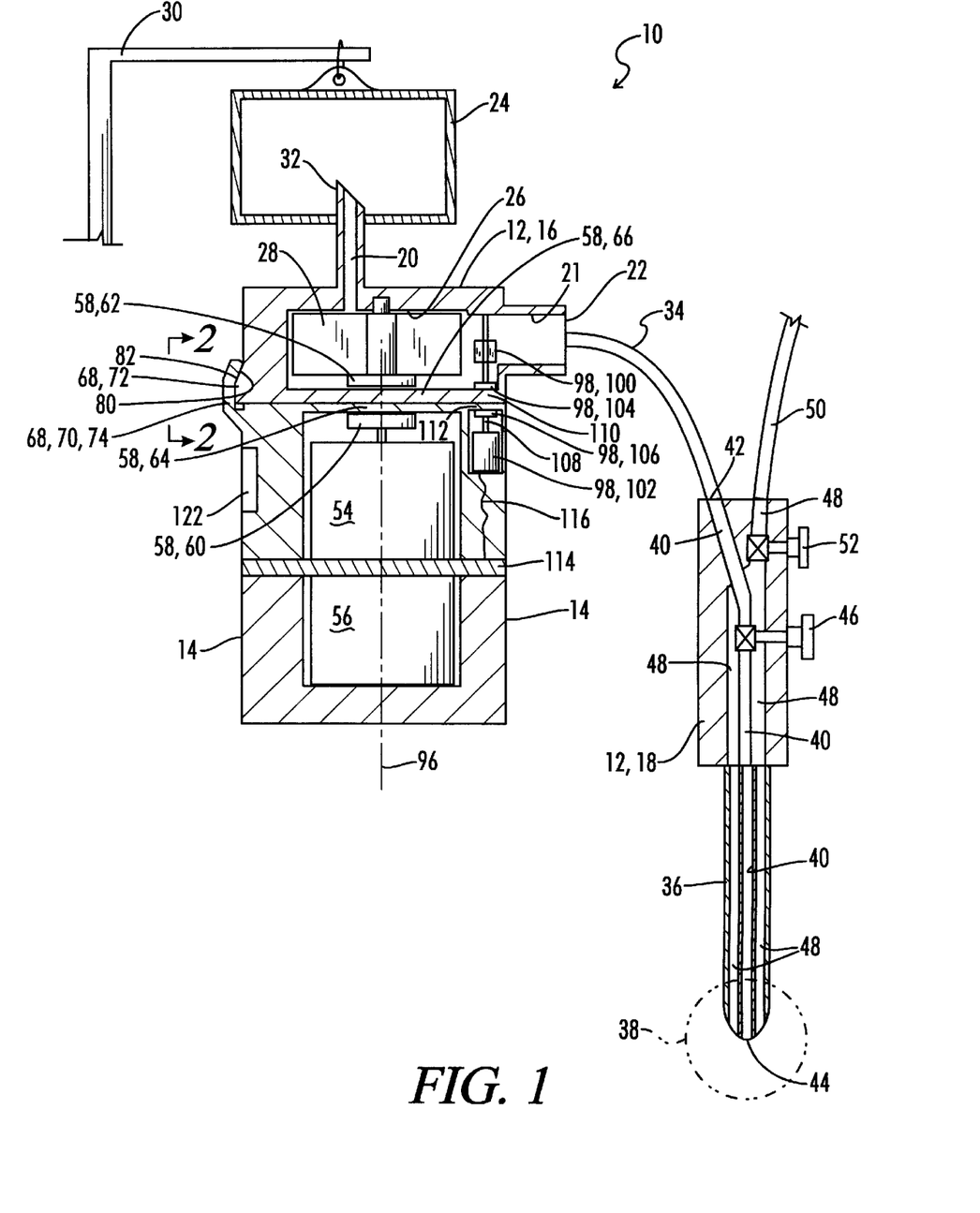
FIG. 1 is a schematic elevation partly sectioned view of the surgical irrigation apparatus of the present invention.

Referring now to the drawings and particularly to FIG. 1, the surgical irrigation apparatus of the present invention is shown and generally designated by the numeral 10. The apparatus 10 includes a disposable assembly 12 and a re-usable assembly 14.

The disposable assembly 12 includes an irrigation fluid pump 16 and a handpiece 18.

The pump 16 has a suction inlet 20 and a discharge outlet 22. A discharge passage 21 leads to outlet 22. The suction inlet 22 communicates a source of irrigation fluid 24 with a pump cavity 26 which has a centrifugal pump impeller 28 disposed rotatably therein.

The irrigation fluid supply 24 is a conventional irrigation fluid bag which is suspended from a conventional support pole 30 such as is used in an operating room. The suction inlet 20 of the pump 16 may be defined in a conventional bayonet-type connector 32 which is inserted in the irrigation fluid supply bag 24 in a known manner.

The discharge outlet 22 of pump 16 is connected to a flexible discharge hose 34 which is connected to the handpiece 12.

The handpiece 12 has an elongated probe 36 extending therefrom to a surgical site 38.

An irrigation fluid supply passage 40 is defined through the handpiece 12 and probe 36 and communicates an irrigation fluid inlet 42 of handpiece 12 with an irrigation fluid outlet 44 of the probe 36. A first manually actuatable valve 46 is included in the handpiece 12 and controls flow of irrigation fluid through the passage 40.

A vacuum passage 48 is also defined through the handpiece 12 and the probe 36. Vacuum passage 48 is connected to a vacuum hose 50 which is connected to a conventional hospital vacuum supply.

A second manually actuatable valve 52 is included in the handpiece 12 and serves to open and close the vacuum passage 48. Preferably the first and second manually actuatable valves 46 and 52 are operable independently of each other.

The re-usable assembly 14 includes a motor 54 and a power source 56. In this embodiment the motor 54 is an electric motor and the power source 56 is a battery.

The apparatus 10 further includes a power transfer and isolation means generally designated by the numeral 58. The power transfer and isolation means 58 provides a means for transferring mechanical power from the motor 54 to the impeller 28 of pump 12 and for isolating irrigation fluid flowing through the pump 12 from contact with the re-usable assembly 14.

In a preferred embodiment, the power transfer and isolation means 58 includes a magnetic coupling having a first magnet 60 and a second magnet 62. The first magnet 60 is connected to the electric motor 54 and is driven thereby. The second magnet 62 is connected to the impeller 28 of pump 12.

The power transfer and isolation means 58 further includes a first impervious wall 64 of the re-usable assembly 14 and a second impervious wall 66 of the disposable assembly 12. The first and second impervious walls 64 and 66 space the first and second magnets 60 and 62 from each other and also provide an impervious means separating the re-usable assembly 14 from the disposable assembly 12 so that sterile irrigation fluid flowing through the pump 16 is not contaminated by the apparatus of the re-usable assembly 14.

A quick connect means 68 is provided for connecting the re-usable assembly 14 to the disposable assembly 12 in a quick, reliable and easy manner in the operating room. The quick connect means 68 can take on many different forms.

Figures 2, 3, 4:
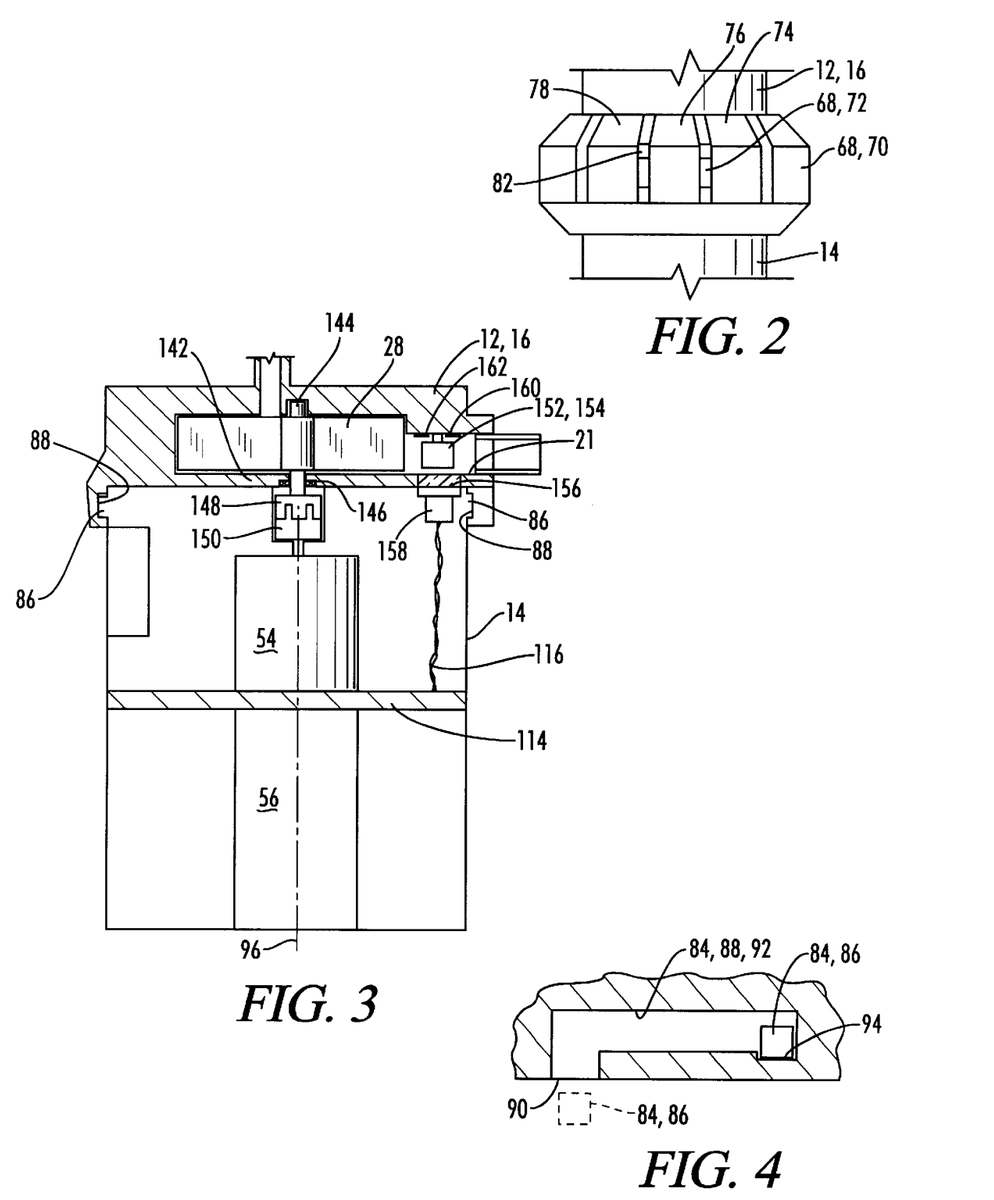
FIG. 2 is a schematic view looking in the direction of line 2—2 of FIG. 1 which illustrates one form of quick connection, namely a collet, between the disposable and re-usable assemblies.
FIG. 3 is a schematic elevation view, similar to FIG. 1, of an alternative embodiment of the disposable and re-usable assemblies. This embodiment illustrates different mechanical connections between motor and pump, different connections between the flow sensor and the re-usable assembly and a different quick connect between the disposable assembly and the re-usable assembly.
FIG. 4 is a schematic laid out view of a lug and slot quick connect as illustrated in FIG. 3.

A first embodiment of the quick connect means 68 is shown in FIGS. 1 and 2 and includes a collet 70 defined on the re-usable assembly 14 and an annular ledge 72 defined on the housing of the pump 16. The collet 70 includes a plurality of resilient fingers such as 74, 76, 78, etc., seen in FIG. 2. Each of the resilient fingers such as finger 74 seen in profile in FIG. 1 includes a first engagement surface 80 defined thereon. The annular ledge 72 has a complementary second engagement surface 82 defined thereon. It will be appreciated that the locations of the collet and the ledge could be reversed to place the collet on the disposable assembly and the ledge on the re-usable assembly.

Thus, the re-usable assembly 14 may be quickly assembled with the disposable assembly 12 by placing the re-usable assembly 14 below the disposable assembly 12 and pushing the re-usable assembly 14 upward so that the fingers such as 78 of collet 70 are biased outward and over the annular ledge 72 and then snapped down in place there over so that the first and second engagement surfaces 80 and 82 are engaged to hold the disposable assembly 12 and re-usable assembly 14 together. The sterile disposable assembly may for example be held by a "clean" nurse, while the re-usable assembly 14 is held by a "dirty" nurse, and the two acting together can quickly connect the components. One of the primary advantages of the present invention is that the re-usable components 14 do not have to be sterilized between usages because they do not come in contact with the irrigation fluid which is being provided to the surgical field.

FIGS. 3 and 4 illustrate an alternative embodiment of a quick connect means which is generally designated by the numeral 84. The quick connect means 84 includes a lug or other protrusion 88 which is defined on the disposable assembly and an arcuate receiving groove 86 which is defined on the re-usable assembly.

As seen on the laid out view of FIG. 4, the receiving groove 88 includes a lower opening 90 through which the lug 86 may be received. The lug 86 then moves through an arcuate horizontal portion 90 and falls into a short recessed groove portion 94 in which it is trapped to hold the disposable assembly and the re-usable assembly together.

As is apparent in FIG. 3, there are preferably at least two such lug and groove arrangements 86 and 88 disposed on diametrically opposite sides of the re-usable assembly. The protrusions 86 and grooves 88 are so arranged and constructed that the disposable assembly and re-usable assembly can be operably connected together by engagement of the lug protrusions 86 with the grooves 88 and a relative rotation of no more than 360° between the disposable assembly and the re-usable assembly. More preferably that rotation is less than 180°.

It will also again be apparent that the locations of the lug and groove could be reversed. As is apparent in both FIGS. 1 and 3, the motor 54 and the pump impeller 18 have aligned axes of rotation defined by a center line 96. Both the collet type quick connect means 68 of FIGS. 1 and 2 and the lug and groove type quick connect means 84 of FIGS. 3 and 4 are annular and define a center thereof coincident with the axis of rotation 96.

Returning now to FIG. 1, the apparatus 10 includes a fluid flow detector means 98 for detecting a flow of irrigation fluid through the pump 16.

Figure 5:
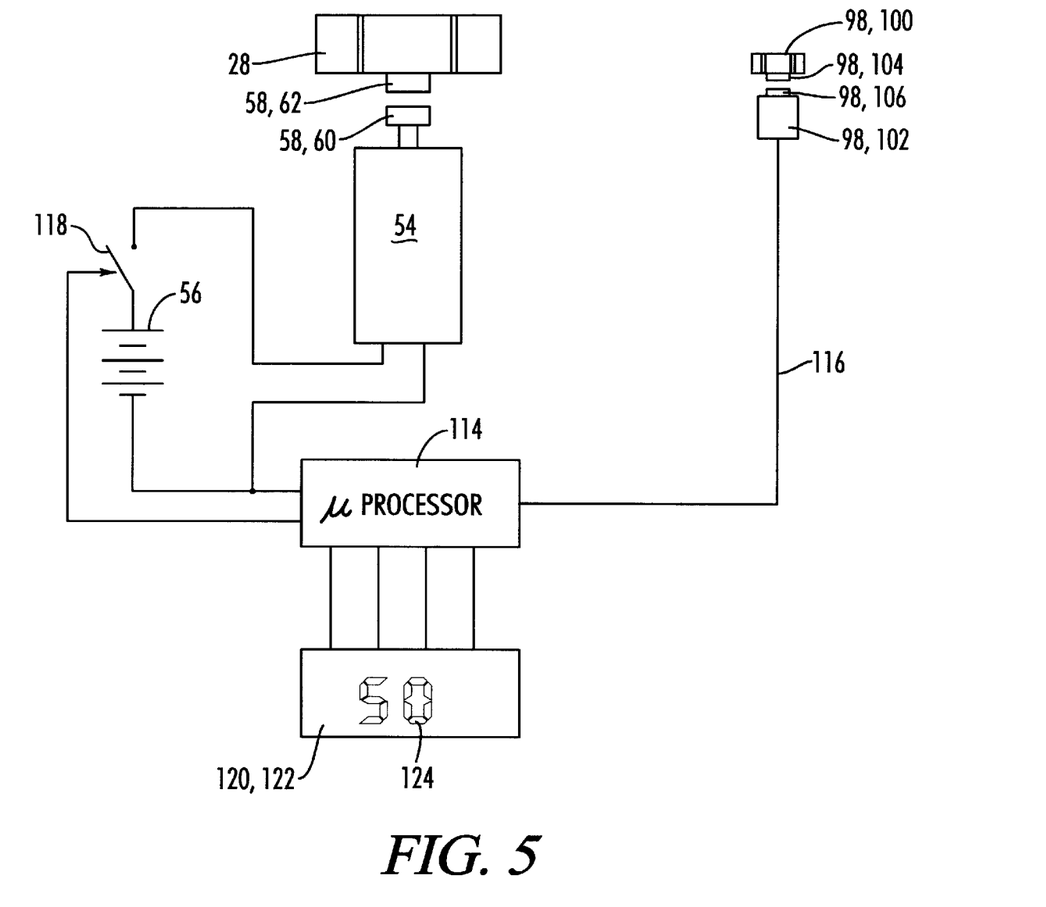
FIG. 5 is a schematic illustration of the electrical power supply and control system.

In a preferred embodiment illustrated in FIGS. 1 and 5, the fluid flow detector means 98 includes an impeller 100 which is disposed in the discharge passage 21 of pump 16 and is so arranged and constructed that the flow of irrigation fluid through the pump 16 turns the impeller 100.

The fluid flow detector means 98 also includes an electromechanical sensor means 102 for converting a mechanical rotation into an electrical signal.

Fluid flow detector means 98 further includes a magnetic coupling including a first magnet 104 attached to the impeller 100 and a second magnet 106 attached to a shaft 108 of the sensor 102. The first and second magnets 104 and 106 are separated from each other by impervious membranes 110 and 112.

The apparatus 10 further includes a microprocessor based control means 114 for turning on the motor 54 in response to detection of fluid flow by the fluid flow detector means 98. The manner of operation of control means 114 is best described with regard to the schematic illustration of FIG. 5.

When the first manually actuatable valve 46 of handpiece 18 is opened, the force of gravity acting upon the irrigation fluid causes irrigation fluid to begin to flow through the pump 16 past the impeller 100. This turns the impeller 100 which in turn turns the first magnet 104. The first magnet 104 causes the second magnet 106 to rotate, thus rotating an electromechanical portion of the sensor 102 and generating an electrical flow indication signal representative of that flowing fluid. The electrical signal is communicated to microprocessor control means 114 over electrical lines 116.

The microprocessor control means 114 senses the flow indicating signal from sensor 102 and sends a control signal to switch 118 causing the switch 118 to close, thus connecting the electric motor 54 to battery 56 and causing the electric motor 54 to begin to rotate.

When the electric motor 54 rotates, that motion is communicated via the magnetic couplings 60, 62 to the centrifugal pump impeller 28 to turn the impeller 28 and begin to pump irrigation fluid under pressure from the pump 16 to the handpiece 12.

The sensor 98 also senses when there is no flow such as when the first valve 46 is closed, and thus sends a signal opening the switch 118 and turning the motor 54 off.

The preferred physical location of the microprocessor control means 114 is schematically illustrated in FIG. 1 as being sandwiched between the motor section 54 and the power supply section 56 of the pump 14.

The microprocessor control means 114 has associated therewith a power supply indication system generally designated by the numeral 120. A system 120 includes a display means 122 for displaying indicia 124 representative of the remaining number of units of power in the battery 56. As is further described below with regard to the logic chart of FIG. 6, each unit of power corresponds to a quantity of power required to conduct one typical surgical procedure with the disposable assembly 12.

Figure 6:
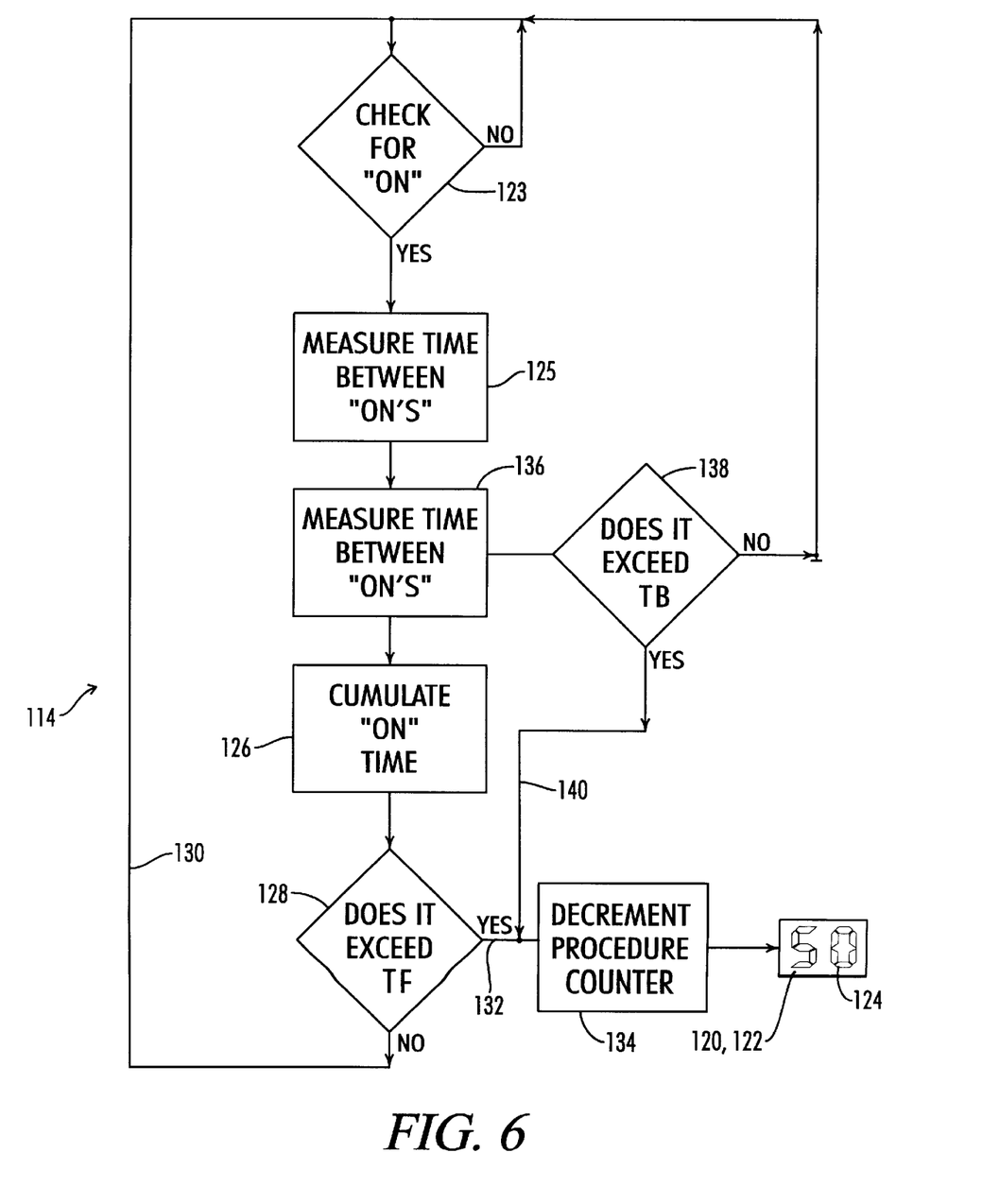
FIG. 6 is a flow chart for the logic of the microprocessor which keeps track of the battery usage time.

FIG. 6 is a logic flow chart illustrating the logic performed by microprocessor control means 114 in association with the power supply indicator system 120.

As represented by block 123, the microprocessor 114 periodically checks to determine whether the switch 118 is closed and the motor 54 is on. If the microprocessor 114 senses that the motor 54 is on, then it measures the time interval for which the motor is on is indicated by block 125. As indicated at block 126, the control system 114 cumulates the "on" times.

Typically the surgeon will open the first valve 46 in short bursts of a few seconds at a time. Then he will open the second valve 52 to suction the surgical field 38.

In block 128, the control system inquires as to whether the cumulated on time exceeds the "TF" which is the standard procedure time.

If the standard procedure time has not been exceeded, then as indicated by logic flow loop 130, the control system 114 continues to monitor for the next time the motor is turned on. The system 114 continues to cumulatively add the "on" time in the manner just described until it determines that the cumulative on time does exceed TF. When the cumulative on time exceeds TF, as indicated by logic flow loop 132, the control system 114 decrements the procedure counter as indicated at logic block 134 which results in a signal to the power supply indication system 120 which decrements the indicia 124.

The logic system of control means 114 also provides a logic block 136 which measures the time between "on" conditions of the motor. If the time between "on" exceeds time TB, which is an indication that the procedure has ended, as indicated at logic block 138, a signal is sent over logic loop 140 to the decrement procedure counter 134 to decrement the indicia 124.

Thus, if a given procedure is completed with less than the total on time TF, the indicia 124 will ultimately be decremented by one unit when logic block 136 determines that the procedure has ended because there is such a long period of time between on conditions of the electric motor.

If, however, a given procedure takes longer than the standard procedure time, TF, the indicia 124 will be decremented at least twice. It will be decremented a first time when the procedure goes beyond time TF for total cumulative one time, and then it will be decremented a second time when the procedure ends and the logic blocks 136, 138 determine that there has been an excessive time between on conditions. Of course, the indicia 124 could be decremented more than twice for an extremely long procedure.

The time between on times TB for determination that the procedure has ended may be, for example, one hour. A typical cumulative on time may be, for example, ten minutes per procedure. For a D size lithium oxide cell battery, a motor current of one amp, and a typical cumulative on time of ten minutes per procedure, the maximum number of procedures which could be conducted with the re-usable assembly 14 is 50 procedures, with a 50% safety factor.

Upon installation of a new power unit, the procedure counter is reset so that it indicates 50 available standard procedure times. The indicia is then decremented when a standard procedure is completed as previously described. Thus, the display indicia shows the number of procedures remaining in the battery capacity.

FIG. 3 is similar to FIG. 1, and illustrates alternative versions of various components of the apparatus. Because both FIGS. 1 and 3 are schematic illustrations, analogous components of FIG. 3 are identified with the same numerals used in FIG. 1, although it will be apparent that in some aspects various of those components have been modified.

The first modification of the apparatus of FIG. 3 as compared to that of FIG. 1 is the difference in the quick connect means 84 as previous described.

There are two other modifications illustrated in FIG. 3. One has to do with the connection between the motor 54 and the pump impeller 28. The other has to do with the means by which the sensor 102 senses flow of irrigation fluid through the pump 16.

In the embodiment of FIG. 3, the disposable assembly 12 includes a wall 142. The impeller 128 of pump 16 is attached to a rotable pump shaft 144 which has an outer end extending through the wall 142. An annular seal 146 is disposed between the pump shaft 144 and the wall 142. A first drive member 148 is attached to the outer end of the pump shaft 144, and a second drive member 150 is attached to the motor 54. The first and second drive members are complementary and engageable by an axial movement of the re-usable assembly 14 toward the disposable assembly 12.

The apparatus of FIG. 3 also includes a different type of fluid flow detection means 152. The flow detection means 152 includes an impeller 154 disposed in the discharge passage 21 of the pump 16. The impeller 54 preferably is constructed so that it will reflect light therefrom, or a mirror 162 could be located behind the rotating impeller so that the impeller interferes with light transmission.

A transparent window 156 is defined in the housing of the pump 16 adjacent reflective impeller 154. A modified sensor 158 is an optical sensor which is capable of transmitting a light wave through the window 156 into the discharge passage 21 where it reflects off the reflective impeller 154 or of a mirror behind the impeller. If the impeller 154 is rotating, an intermittent reflective signal will pass back through window 156 and be picked up by sensor 158. The resulting signal is transmitted over lines 116 to microprocessor 114.

In a modified version of the flow detection means just described, the light beam may originate from a light emitting diode 160 located behind the rotating impeller 154. In either event a light beam passes from inside the pump through the transparent window 156 to the sensor 158.

Figure 7:
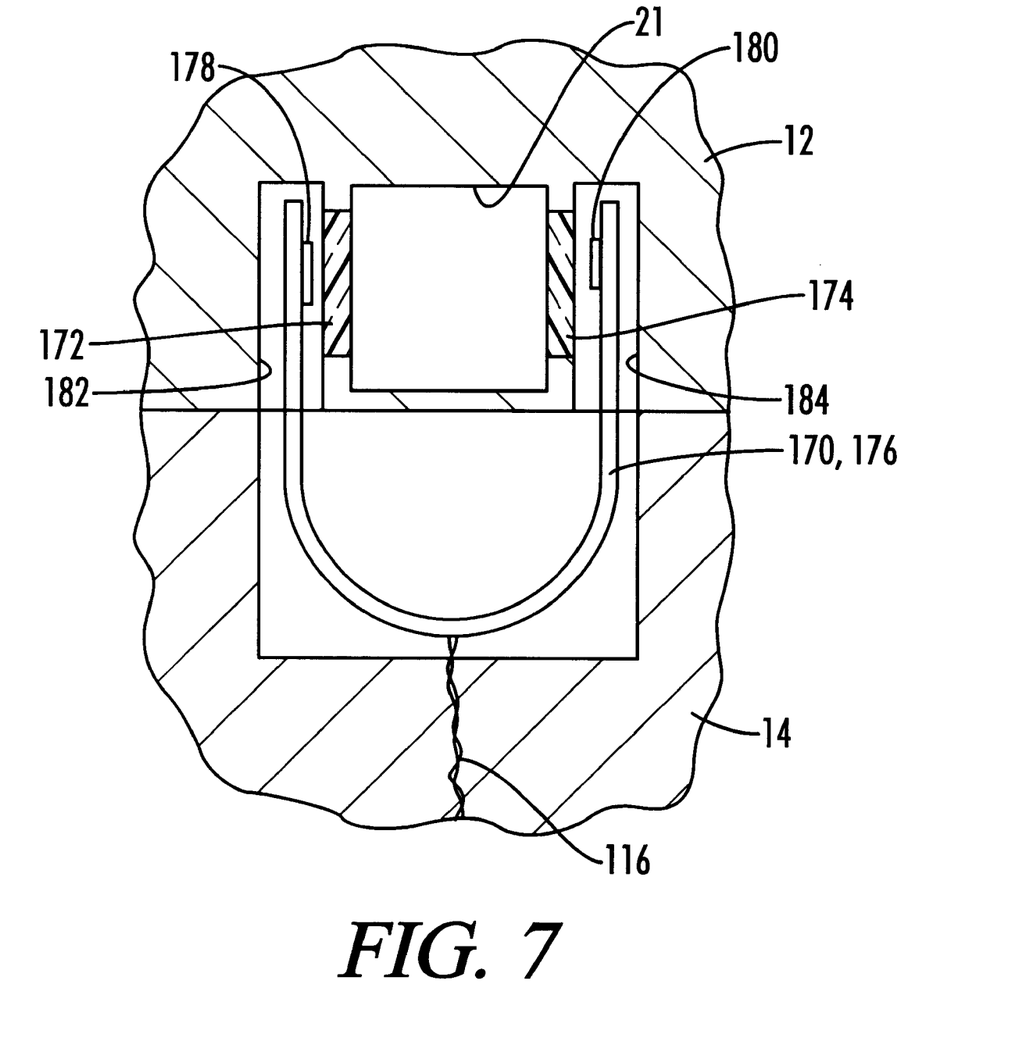
FIG. 7 is a schematic sectioned view of another alternative construction for the sensor which senses flow of fluid in the pump.

Another alternative sensor means 170 is illustrated in FIG. 7. In FIG. 7 the disposable assembly 12 includes two transparent windows 172 and 174 on opposite sides of the discharge passage 21.

The sensor 170 includes a U-shape frame 176 having light emitter 178 and a light receiver 180 carried thereby. The arms of frame 176, the emitter 178 and the receiver 180 are received in cavities 182 and 184 of the disposable assembly 12. Frame 176 is mounted in reusable assembly 14. The sensor 170 is connected to microprocessor 114 by wires 116.

Emitter 178 emits a light signal which passes through window 172, discharge passage 21 and then window 174. The light signal is received by receiver 180. Anything which interferes with the signal received by receiver 180 will generate a changing electrical signal which is transmitted to microprocessor 114.

The light beam passing from transmitter 178 to receiver 180 can be interfered with in many ways correlated to the flow of fluid. In the simplest embodiment the simple change from stagnant fluid to flowing fluid will affect the light beam due to the boundary layers which are created when the fluid begins to flow. Also an impeller similar to impeller 154 of FIG. 3 could be placed between transmitter 178 and receiver 180.

Still another alternative for the flow sensor means is to sense the change in pressure within the pump when the valve 46 is opened.

Methods

A method of using the surgical irrigation apparatus 10 to supply irrigation fluid to the surgical site 38 during a surgical procedure includes the following steps.

First the sterile disposable assembly 12 is provided, including the irrigation fluid pump 16. Also, a re-usable assembly 14 is provided, including the motor 54.

The re-usable assembly 14 is then connected to the sterile disposable assembly 12 through use of the quick connect means 68 or 84.

Then power is transferred from motor 54 to the pump 16 via transfer of force from the first magnet 60 to the second magnet 62, thereby pumping irrigation fluid from the source 24 to the handpiece 12 with the pump 16. During the time that the irrigation fluid is flowing through the pump, that irrigation fluid, which is sterile, is isolated from the re-usable assembly 14 by the impermeable walls 64 and 66 which separate the magnets 60 and 62 so that it will not be contaminated thereby.

After the surgical procedure, the disposable assembly 12 can be easily disconnected from the re-usable assembly 14 and disposed of Then the re-usable assembly 14 may be connected to another disposable assembly 12 and irrigation fluid can be supplied for another surgical procedure.

When the apparatus 10 is first placed in use, the motor 54 is off and both of the manually actuatable valves 52 and 46 are biased to a closed position.

The surgeon then opens the first manually actuatable valve 46 and the force of gravity acting upon the irrigation fluid in source 24 causes the irrigation fluid to begin flowing downward through the pump 16 and through the supply hose 34 to the handpiece 12.

Very rapidly, upon the beginning of the flow, the fluid flow detector means 98 detects the flow of irrigation fluid through the pump 16.

When the irrigation fluid first begins to flow through the discharge outlet of pump 16, it rotates the impeller 100. That rotational motion of impeller 100 is transmitted to the electromechanical sensor 102 via the magnetic coupling 104, 106. When the sensor 102 is rotated, it generates an electrical signal.

In the alternative embodiments of FIG. 3 or FIG. 7, the sensor senses a light signal which passes through a transparent window and which is correlated to flow of fluid through the discharge passage 21.

As noted, another alternative is to sense a pressure change within the pump.

The microprocessor based control means 114 then rapidly closes the switch 118 thus providing power to motor 54, turning motor 54 on. When the motor 54 turns on, it begins rotating the centrifugal pump impeller 28 which then pumps irrigation fluid under pressure from the source 24 to the handpiece 12.

In a preferred embodiment, the sensor device 98 can detect flow and will typically turn on the motor 54 within less than 2.0 seconds of the opening of valve 46, and preferably within less than 0.1 second.

When the surgeon releases the valve 46 so that it can spring back to a closed position, the flow detector means 98 will sense that flow has stopped and will open the switch 56 thus turning the motor 54 off.

Thus, it is seen that the apparatus and methods of the present invention readily achieve the ends and advantages mentioned as well as those inherent therein. While certain preferred embodiments of the invention have been illustrated and described for purposes of the present disclosure, numerous changes in the arrangement and construction of parts and steps may be made by those skilled in the art, which changes are encompassed within the scope and spirit of the present invention as defined by the appended claims.

What is claimed is:

1. A surgical irrigation apparatus, comprising:
    a disposable assembly, including an irrigation fluid pump and a handpiece having a supply passage for delivering irrigation fluid to a surgical site, said handpiece including a first manually actuatable valve disposed in said supply passage;
    a re-useable assembly, including a motor and a power source;
    a fluid flow detector for detecting a flow of irrigation fluid through said pump in response to the opening of the valve;
    a controller for turning on said motor in response to detection of fluid flow by said fluid flow detector; and
    a power transfer and isolation coupling for transferring mechanical power from said motor to said pump and for isolating said irrigation fluid flowing through said pump from contact with said re-usable assembly.

2. The apparatus of claim 1, wherein:
    said power transfer and isolation coupling includes a magnetic coupling including a first magnet connected to said motor and a second magnet connected to said pump, said first and second magnets being spaced from each other.

3. The apparatus of claim 2, wherein:

said power transfer and isolation coupling further includes an impervious wall separating said first and second magnets.

4. The apparatus of claim 1, wherein:

at least one of said disposable assembly and said re-usable assembly includes an impervious wall separating said motor from said pump.

5. The apparatus of claim 1, further comprising:

a quick-connect for connecting said re-usable assembly to said disposable assembly.

6. The apparatus of claim 5, wherein said quick-connect comprises:

a collet defined on one of said disposable assembly and said re-usable assembly, said collet including at least one resilient finger having a first engagement surface defined thereon; and a complementary second engagement surface defined on the other of said disposable assembly and said re-usable assembly, said first and second engagement surfaces being shaped and arranged for resilient locking engagement with each other when said disposable assembly is pushed into operable engagement with said re-usable assembly.

7. The apparatus of claim 5, wherein said quick-connects comprises:

a protrusion defined on one of said disposable assembly and said re-usable assembly; and an arcuate receiving groove defined on the other of said disposable assembly and said re-usable assembly, said protrusion and said groove being so arranged and constructed that said disposable assembly and said re-usable assembly can be operably connected together by engagement of said protrusion with said groove and a relative rotation of no more than 360° between said disposable assembly and said re-usable assembly.

8. The apparatus of claim 5, wherein:

said motor and said pump have aligned axes of rotation; and said quick-connect is annular and defines a center thereof coincident with said axes of rotation.

9. The apparatus of claim 1, wherein:

said disposable assembly includes a wall;

said pump includes a rotatable pump shaft having an outer end extending through said wall;

said power transfer and isolation coupling includes:
an annular seal between said pump shaft and said wall;
a first drive member attached to said outer end of said pump shaft; and
a second drive member attached to said motor, said first and second drive members being complementary and engageable by an axial movement of said re-usable assembly toward said disposable assembly.

10. The apparatus of claim 1 wherein said handpiece further comprises:

a vacuum passage for communicating the surgical site with a vacuum; and a second manually actuatable valve disposed in said vacuum passage.

11. The apparatus of claim 10, wherein:

said second valve is operable independent of said first valve.

12. The apparatus of claim 1, wherein said fluid flow detector comprises:

an impeller disposed in said pump and so arranged and constructed that the flow of irrigation fluid through said pump turns said impeller;

a sensor for converting a mechanical rotation into an electrical signal; and a first magnetic coupling between said impeller and said sensor.

13. The apparatus of claim 12, wherein;

said power transfer and isolation coupling includes a second magnetic coupling between said motor and said pump.

14. The apparatus of claim 1, wherein:

said pump has an irrigation fluid flow passage defined therethrough; and said fluid flow detector comprises:
a transparent window included in said disposable assembly and communicated with said fluid flow passage; and
an optical sensor included in said re-usable assembly and arranged to receive a light signal through said transparent window.

15. The apparatus of claim 1, further comprising: a power supply indication system, including:

a display for displaying an indicia representative of a remaining number of units of power in said power source, each unit corresponding to a quantity of power required to conduct one typical surgical procedure with said disposable assembly;

a sensor for sensing when said disposable assembly has completed a surgical procedure; and a decrementing system for reducing said indicia of said display in response to said sensor.

16. The apparatus of claim 1, wherein:

said disposable assembly includes no electrical components; and all electrical components of said apparatus are contained in said re-usable assembly.

17. The apparatus of claim 1, wherein the power source is a battery.

18. A surgical irrigation apparatus, comprising:

a pump, including a suction inlet for connection to an irrigation fluid source, a discharge outlet, and a flow passage communicating said inlet and outlet;

a motor operatively connected to said pump;

a handpiece having a supply passage for delivering the irrigation fluid to a surgical site, said handpiece including a manually actuatable valve disposed in said supply passage;

a conduit connecting said discharge outlet of said pump to said supply passage of said handpiece;

a flow detector for generating a flow indication signal in response to flow of the irrigation fluid through said pump when said valve is initially opened; and a controller, operatively connected to said flow detector, for generating a control signal to turn on said motor and activate said pump in response to said flow indication signal.

19. The apparatus of claim 18, wherein said flow detector comprises:

an impeller disposed in said pump;

a sensor for converting a mechanical rotation into an electrical signal, said electrical signal being said flow indication signal; and a magnetic coupling between said impeller and said sensor.

20. The apparatus of claim 18, wherein said flow detector comprises:
a transparent window included in said pump and communicated with said flow passage; and
an optical sensor associated with said motor, and arranged to receive a light signal through said transparent window.

21. A method of supplying irrigation fluid to a surgical site during a surgical procedure, said method comprising the steps of:
(a) providing a sterile disposable assembly including an irrigation fluid pump;
(b) providing a re-usable assembly including a motor;
(c) connecting the re-usable assembly to the sterile disposable assembly;
(d) transferring power from the motor to the pump and thereby pumping irrigation fluid to the surgical site;
(e) during step (d), isolating irrigation fluid flowing through the pump to the surgical site from contact with the re-usable assembly; and wherein
said step (a) is further characterized in that the disposable assembly includes a handpiece having a supply passage for directing irrigation fluid to the surgical site; and includes a valve controlling flow through the supply passage; and
said method further includes the steps of:
opening the valve;
initially flowing irrigation fluid through the pump and the supply passage by gravity induced flow;
detecting the flow of irrigation fluids through the pump; and
turning on the motor and the pump in response to said detecting step.

22. The method of claim 21, further comprising:
after the surgical procedure, disconnecting the disposable assembly from the re-usable assembly and then disposing of said disposable assembly;
connecting the re-usable assembly to another disposable assembly; and
supplying irrigation fluid for another surgical procedure.

23. The method of claim 21, wherein:
said step (d) includes transferring magnetic force from a first magnet attached to said motor to a second magnet attached to said pump; and
said step (e) includes providing an impermeable wall separating said first and second magnets.

24. The method of claim 21, wherein said detecting step further comprises:
rotating an impeller disposed in the pump with the flowing irrigation fluid;
transmitting the rotational motion of the impeller to an electromechanical sensor; and
generating an electric signal in said electromechanical sensor.

25. The method of claim 21, Wherein said detecting step further comprises:
passing a light signal through a transparent window of the pump, said light signal being correlated to flow of irrigation fluid through the pump; and
receiving said light signal in an optical sensor disposed in the re-usable assembly.

26. A method of actuating a surgical irrigation system, said method comprising of the steps of:
(a) manually opening an irrigation fluid supply valve in a handpiece;
(b) after step (a), initially flowing irrigation fluid by gravity flow from a fluid source through an unactivated pump;
(c) during step (b) sensing said gravity flow of irrigation fluid;
(d) in response to step (c), turning on a motor connected to the pump;
(e) thereby powering the pump and pumping pressurized irrigation fluid to the handpiece.

27. The method of 26, wherein
said step (d) occurs within 0.1 second after said step (a).

28. The method of claim 26, wherein said step (c) comprises:
rotating an impeller disposed in the pump with the flowing irrigation fluid;
transmitting the rotational motion of the impeller to an electromechanical sensor; and
generating an electric signal in said electromechanical sensor.

29. The method of claim 26, wherein said step (c) comprises:
passing a light signal through a transparent window disposed in the pump; and receiving said light signal in an optical sensor disposed outside the pump.

30. A surgical irrigation apparatus, comprising:
a disposable assembly, including an irrigation pump and a handpiece having a supply passage for delivering irrigation fluid to a surgical site;
a reusable assembly, including a motor and power source;
a power transfer and isolation coupling for transferring mechanical power from said motor to said pump and for isolating said irrigation fluid flowing through said pump from contact with said reusable assembly; and
a power supply indication system including:
a display for displaying an indicia representative of a remaining number of units of power in said power source, each unit corresponding to a quantity of power required to conduct one typical surgical procedure with said disposable assembly;
a sensor for sensing when said disposable assembly has completed a surgical procedure; and
a decrementing system for reducing said indicia of said display in response to said sensor.

31. A method of supplying irrigation fluid to a surgical site during a surgical procedure, said method comprising the steps of:
(a) providing a sterile disposable assembly including an irrigation fluid pump;
(b) providing a reusable assembly including a motor;
(c) connecting the reusable assembly to the sterile disposable assembly;
(d) transferring power from the motor to the pump by transferring magnetic force from a first magnet attached to said motor to a second magnet attached to said pump, and thereby pumping irrigation fluid to the surgical site; and
(e) during step (d), isolating irrigation fluid flowing through the pump to the surgical site from contact with the reusable assembly by providing an impermeable wall separating said first and second magnets.

* * * * *